United States Patent
Frantz

(10) Patent No.: US 7,535,793 B2
(45) Date of Patent: May 19, 2009

(54) ACOUSTO-MECHANICAL VEHICLE CHARACTERIZATION SYSTEM AND METHOD

(76) Inventor: Robert H. Frantz, P.O. Box 23324, Oklahoma City, OK (US) 73123

(\*) Notice: Subject to any disclaimer, the term of this patent is extended or adjusted under 35 U.S.C. 154(b) by 406 days.

(21) Appl. No.: 11/471,256

(22) Filed: Jun. 20, 2006

(65) Prior Publication Data

US 2007/0019839 A1 Jan. 25, 2007

Related U.S. Application Data

(60) Provisional application No. 60/693,318, filed on Jun. 23, 2005.

(51) Int. Cl.
*H04B 17/00* (2006.01)
(52) U.S. Cl. ....................................... 367/13
(58) Field of Classification Search ................... 367/13; 73/597, 290 V
See application file for complete search history.

(56) References Cited

U.S. PATENT DOCUMENTS

| | | | |
|---|---|---|---|
| 5,410,604 A | 4/1995 | Saito et al. | |
| 5,416,844 A | 5/1995 | Nakaji et al. | |
| 5,929,337 A * | 7/1999 | Collins et al. | 73/597 |
| 6,234,023 B1 * | 5/2001 | Collins et al. | 73/290 V |
| 7,265,662 B2 * | 9/2007 | Belanger | 340/521 |

OTHER PUBLICATIONS

"SIM System II: Acoustic Test and Measurement System", downloaded from http://www.meyersound.com/products/software/sim/index2/htm on Jun. 22, 2005.
Laurent, M., "Automotive Engineer PLUS Software—LMS Engineering", downloaded from http://www.ae-plus.com/Key%20topics/kt-software-news9.htm on Jun. 22, 2005.
"Audio Spectrum Analyzer and Acoustics Software", downloaded from http://www.purebits.com on Jun. 22, 2006.
Guidata, S., Sottek, R. & Genuit K., "HEAD Acoustics-News-DAGA 2003, List of Lectures", downloaded from http://www.head-acoustics.de/7news/N-DAGAlist04-e.htm on Jun. 22, 2005.

(Continued)

*Primary Examiner*—Ian J Lobo
(74) *Attorney, Agent, or Firm*—Robert H. Frantz

(57) ABSTRACT

A system and method for detecting concealed cargo, such as explosives contained in a closed vehicle trunk, by characterizing the transfer function between sets of wheels of the vehicle and automatically detecting changes of transfer functions due to changes in mass loading. The system and method contacts a first tire of the vehicle and transduces a signal such as a sweeping acoustic signal into the vehicle, simultaneously collecting the signal transmitted and attenuated through the vehicle to an second tire. The collected signal is analyzed and compared to previous transfer function characterization results to detect significant changes in the transfer function. If a significant change is detected, a system operator is alerted to prompt further preemptive action, such as a full search of the vehicle.

15 Claims, 13 Drawing Sheets

OTHER PUBLICATIONS

Ryu, Y., "Test Procedure and User Interface for Determination of Acoustic Properties of Materials using the Two-microphone Transfer Function Method", downloaded from http://www.ingentaconnect.com on Jun. 22, 2005.

"Mechanical Acoustics/Vibration Engineering—Modal test of composite", downloaded from http://www.eng-tips.com/viewthread.cfm?qid=125400&page=1 on Jun. 22, 2005.

"Mechanical Acoustics/Vibration Engineering—Transfer function from time-domain data in sweep test" from http://www.eng-tips.com/viewthread.cfm?qid=103887&page=9 on Jun. 22, 2005.

"Mechanical Acoustics/Vibration Engineering—Transfer Function Filter", downloaded from http://www.eng-tips.com/viewthread.cfm?qid=122934&page=2 on Jun. 22, 2005.

* cited by examiner

ACOUSTO-MECHANICAL VEHICLE CHARACTERIZATION SYSTEM AND METHOD

This patent application is related to, and claims benefit under 35 U.S.C. §119(e) to U.S. provisional patent application Ser. No. 60/693,318, filed on Jun. 23, 2005, by Robert H. Frantz.

BACKGROUND OF THE INVENTION

1. Field of the Invention

This invention relates to technologies to characterize and unintrusively search the structure and contents of a vehicle, and especially to searching the contents of a closed vehicle trunk or cargo area.

2. Background of the Invention

Vehicles, and especially cars, are often used to transport illegal materials, including but not limited to explosive materials. Often, these materials are transported in a closed trunk area of a car, or in a box or under a tarp in the tailgate area of a station wagon.

Depending on the legal jurisdiction and practical environmental considerations, it may not be allowable or possible to physically search every vehicle by opening the trunk or hatchback to find and deter such transportation. In some situations, the hatches or trunk lids to vehicles carrying explosives have been "booby trapped" such that the explosives will be detonated upon opening the hatch or lid. Failure to preemptively detect such materials, however, can have catastrophic results, including the successful detonation of a car bomb near an entrance to a military base or reserve, police station, government facility, hotel, or entertainment center.

The most common technology currently deployed to search closed vehicle trunks and cargo areas without opening them is to irradiate the vehicle and collect the transmitted radiation or scattered radiation for analysis. This approach has several drawbacks, including expense, health concerns for the operators, and size of the machines.

Therefore, there is a need in the art for an unintrusive system and method for searching a closed vehicle trunk or cargo area.

SUMMARY OF THE INVENTION

The present invention characterizes a vehicle according to its transfer functions between one or more pairs of tires and wheels, preferably across a spectrum of signal frequencies such as the acoustic spectrum. When a vehicle component is significantly modified, such as adding weight to a portion of the vehicle, the measured transfer functions will change. In some situations, the change to the measured transfer functions will change predictably, such as in a certain frequency range for liquids, and in another frequency range for solids or semi-solids.

The invention may be provided in a "speed bump" style casing, or buried level with grade of a vehicle passageway, such that when two wheels, such as the two rear wheels, of a vehicle simultaneously rest upon it, a transducer sends a signal into one wheel while a sensor receives the attenuated signal at the other wheel. In another embodiment, a platform is provided on which an entire vehicle may rest, such that all three or more wheels of the vehicle can be used as points of signal transduction and signal sensing. As such, the invention may perform signal transfer function analysis between two or more sets of wheels of the vehicle.

Once a vehicle has been characterized at least once, its characterizations are stored in a networked data storage, such as a database on a computer network. During subsequent characterizations of the same vehicle, the current transfer function data is automatically compared to one or more previously stored data sets, and any anomalies are indicated to the operator of the system such that preemptive action may be taken (e.g. quarantine of the vehicle until search is complete, detainment of operator, raising of blast shields, etc.).

BRIEF DESCRIPTION OF THE FIGURES

The following detailed description when taken in conjunction with the figures presented herein provide a complete disclosure of the invention.

DETAILED DESCRIPTION OF THE INVENTION

The present invention utilizes mechanical energy to detect changes to the structure, including addition of liquid, solid, or semi-solid (e.g. "plastic") cargo, without requiring the opening of storage doors, hoods, hatches, or trunk lids. One or more signal transducers are placed in contact with at least one tire of the vehicle, preferably by driving the vehicle upon a housing of the invention. A signal, preferably a sweeping frequency signal, is induced into the vehicle from the transducer, while simultaneously measuring signal characteristics, such as signal amplitude and/or phase, presented at another wheel of the same vehicle.

Preferably, a sweeping signal from 0 Hz to 50 kHz is employed, which is generally known to be transmitted and attenuated by different materials differently. For example, some liquids will transfer certain frequencies with very little attenuation, while some solids such as steel will transfer other frequencies with little attenuation. Shape and size of each portion of the vehicle also cause certain frequency-attenuation characteristics to be present for each vehicle make and model.

According to one aspect of the present invention, it is not necessary to know the precise frequency transfer characteristics of every possible material, shape and size, in order to perform a detection of a change in the vehicle's configuration. Rather, every vehicle's complex transfer characteristics are initially characterized and stored. Later, during a subsequent scan of the same vehicle, the current characteristics are compared to one or more previously captured scans, and if any significant changes are found, the operator of the system is alerted.

Figure 9:
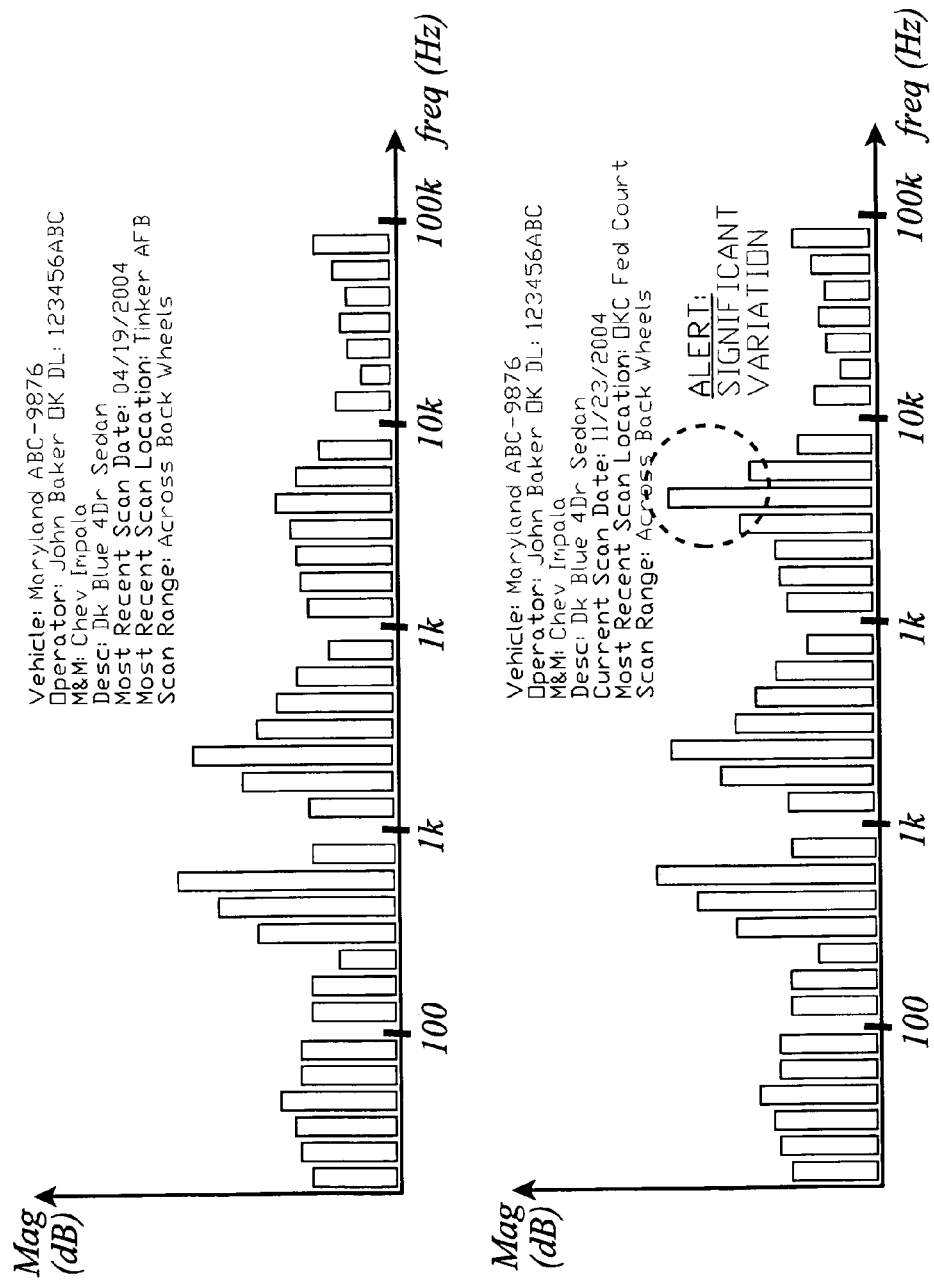
FIG. 9 illustrates a display to an operator according to the invention.

For example, a particular car is initially scanned as it enters a military base, having an empty trunk, and about half a tank full of gasoline. This car will initially present a certain frequency-attenuation profile (95), as shown in FIG. 9. Later, if the car is scanned upon entry of another (or the same) facility, if the gasoline tank is completely full, and the trunk is loaded with cargo, its transfer characteristics will be affected, and its frequency-attenuation profile (96) will show differences (97) from its earlier scan. This may be an indication of nothing more than a fuller gas tank and a box of books in the trunk, or it may be an indication of a trunk loaded with explosives and a liquid accelerant. Therefore, the user or operator of the invention is alerted to the difference so that preemptive action may be taken.

Because all of the components of the vehicle are in series and parallel with the other components, variations of the vehicle not only in the trunk or cargo area may be detected, including but not limited to:

(1) the cavities of pneumatic tires, including a spare tire;
(2) cushions of seats;
(3) the fuel tanks;
(4) cavities of mufflers and pipes; and
(5) hidden compartments and spaces such as under the dashboard.

System Architecture

Figure 1:
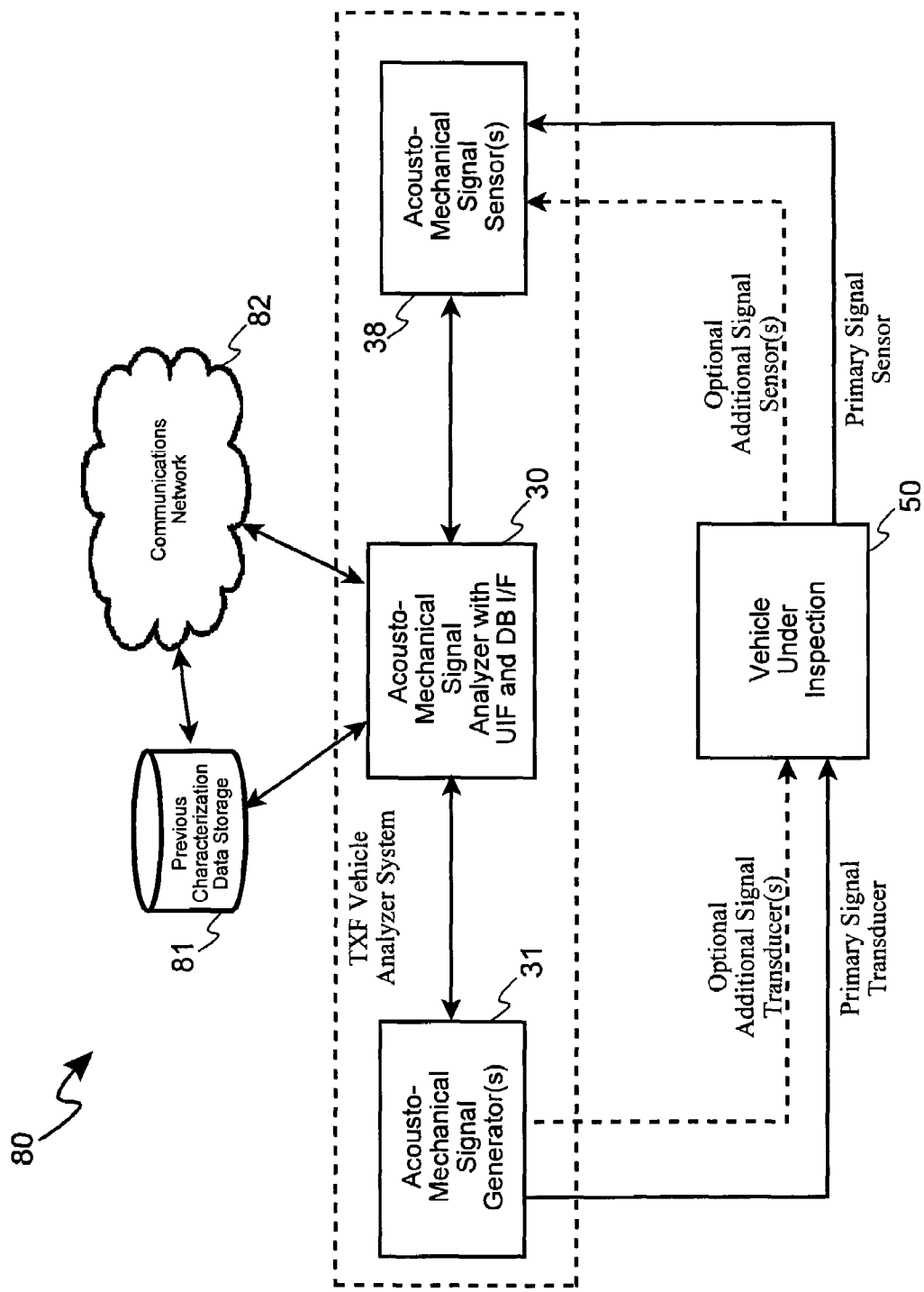
FIG. 1 shows the arrangement of the invention's major components.

Turning to FIG. 1, an architecture of system components according to the present invention is shown. A signal analyzer (30) is coupled in a controlling arrangement with one or more signal generators (31) and one or more matching signal sensors. The analyzer (30) also has a user interface, such as a computer display with keyboard and mouse, and an interface to a storage system (81), such as a remote database interface via a computer network (82). More details of each component, and their cooperative interaction, will be present in the following paragraphs.

The signal generator and sensors are coupled to a vehicle in order to induce the excitation energy, and to measure the transfer of the excitation energy through the vehicle. One embodiment of the invention induces acoustic or vibrational energy into an object using air as the coupling mechanism, such as using a large speaker spaced a distance from a side or surface of the vehicle. Microphones are also spaced a distance from the vehicle, in an arrangement which places the vehicle between the speakers and microphones, or which places the vehicle in an arrangement such that reflected energy from the vehicle is collected by the microphones. Multiple sets of microphones may allow both configurations to be realized in the same test area. Such an indirectly couple embodiment is capable of measuring acoustic or vibrational characteristics of the vehicle including, but not limited to, its absorption and reflection coefficients, and its surface reflection and admittance.

According to another embodiment, the excitation energy is directly coupled to the vehicle through one or more vehicle structural components, such as one or more tires, and the sensors receive the transferred energy through directly coupling to one or more vehicle structural components, such as one or more tires. Alternate vehicle components can be used for coupling, such as bumpers, side panels, etc., as well.

Figure 7A:
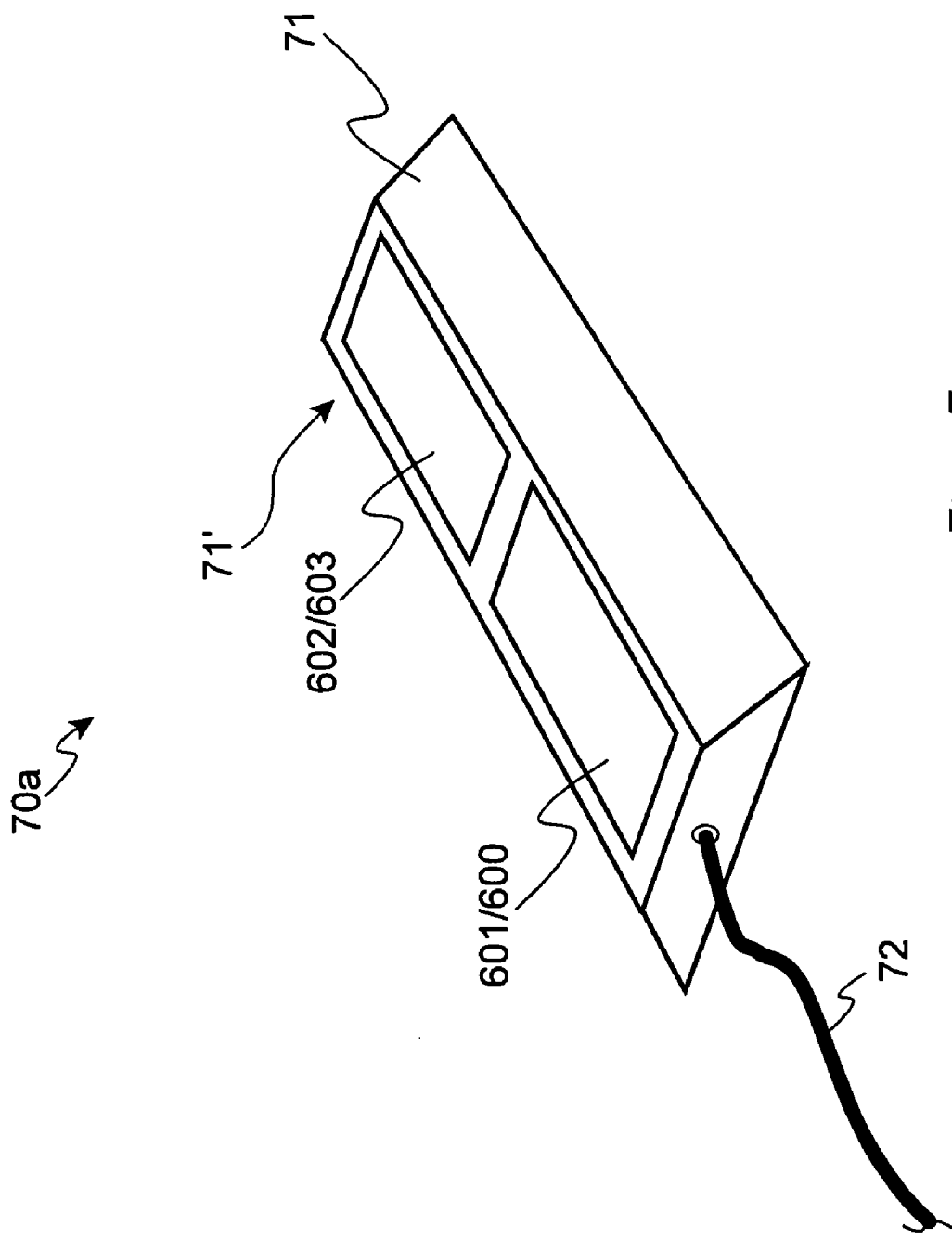
FIG. 7a shows a "speed bump" style embodiment of the invention, capable of performing transfer function characterization between two front wheels or two back wheels.
Figure 7B:
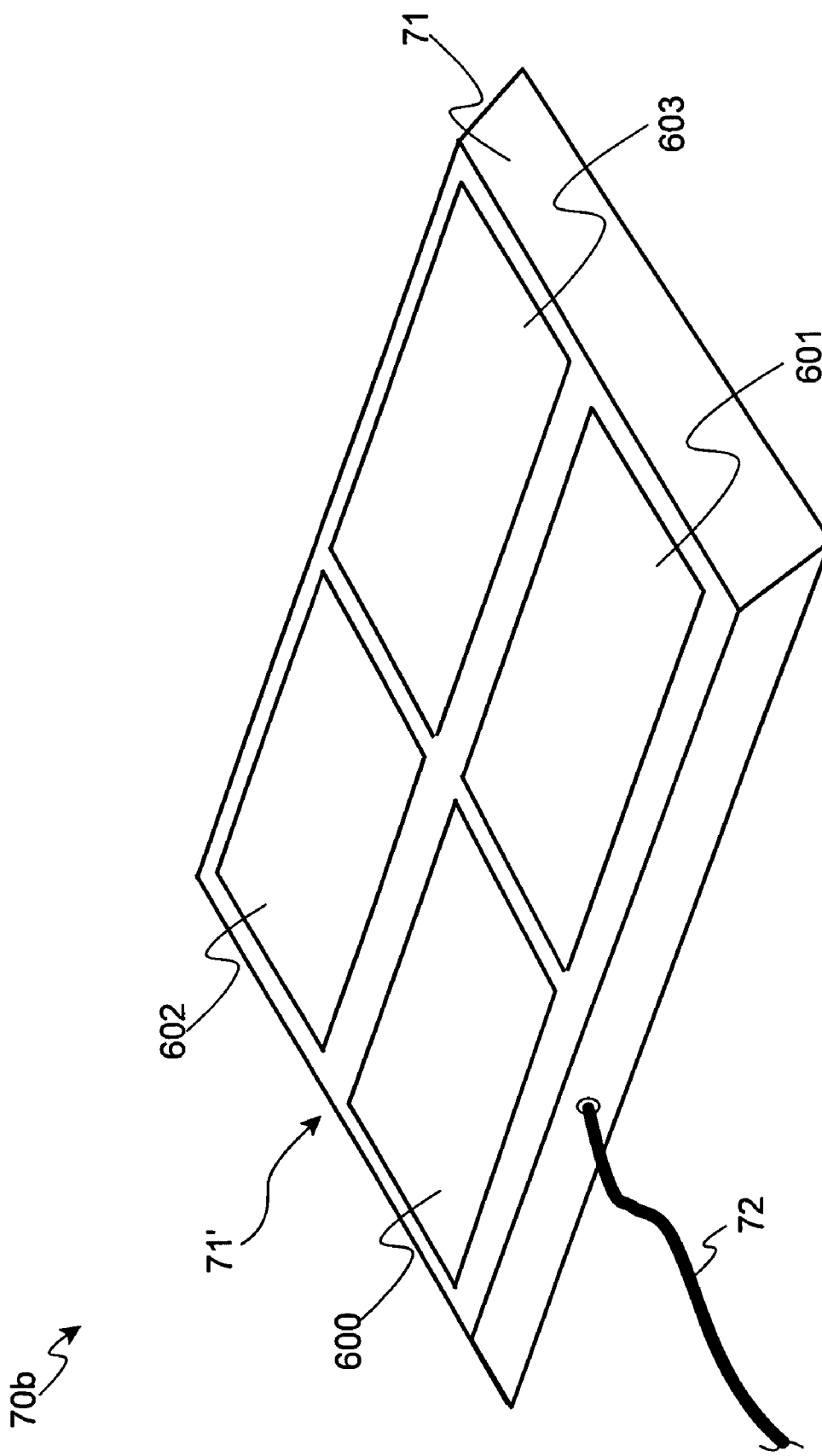
FIG. 7b shows a "platform" style embodiment of the invention, capable of performing multiple transfer function characterization between two front wheels, two back wheels, or a selection of a front wheel and a back wheel.

For the purposes of presenting an exemplary embodiment of the invention, an embodiment is disclosed in the following paragraphs which couples energy to and from the vehicle under inspection (50) using two or more tires via mechanical interface such as a drive-over or drive-on speed bump or platform, as shown in FIGS. 7a and 7b, respectively. Each of these housings provide an approach ramp (71) upon which a vehicle drives, across a top surface, and down a departure ramp (71'). In one embodiment (7a), a left wheel plate (601/600) provides mechanical interface to the left rear and/or left front tires at the appropriate instance of the vehicle passing over it. Likewise, a right wheel plate (602/603) provides mechanical interface to the right rear and/or right front tires at the appropriate instance of the vehicle passing over it. In another embodiment (7b), a platform is provided which is divided into quadrants, each of which is provided with a mechanical interface plate for contacting a vehicle tire (600, 601, 602, 603), while the vehicle passes over the platform or rests on the platform.

In both configurations, one or more mechanical signal generators such as "shakers", "vibrators" or heavy speaker voice coils are provided under one or more plates such that a mechanical signal can be induced into the vehicle via the plate, under the control of the analyzer (30). Similarly, one or more signal sensors are provided under one or more plates to receive attenuated signals from the vehicle through one or more tires. The sensed attenuated signals are returned to the analyzer (30) for frequency, phase and amplitude analysis.

Transfer Function Models of the Vehicle Components

Figure 5:
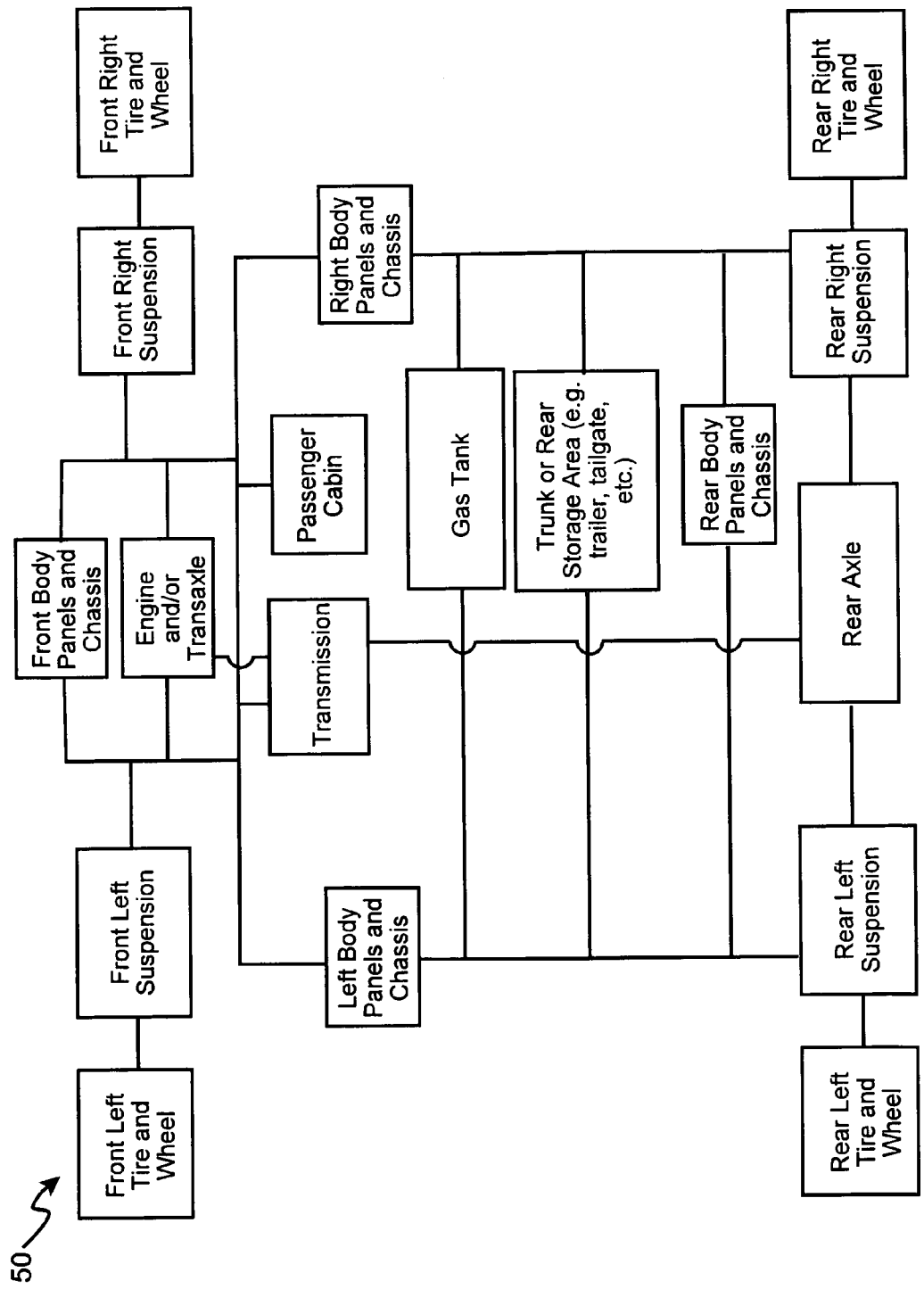
FIG. 5 illustrates a more complete impedance or transfer function topology of a typical vehicle.

Turning to FIG. 5, the major components of a vehicle are shown in a topology according to the typical paths that they communicate vibrational and mechanical energy, including the tires, suspension components, body panels, engine, transaxle and/or transmission (both in the case of four-wheel drive vehicle), passenger cabin, fuel tank, chassis, cargo and storage areas, and axle(s). In a mathematical sense, each of the boxes shown in FIG. 5 can be replaced with a frequency-dependent transfer function $Z^{-1}(f)$, if known. Even if a specific transfer function for a specific component is unknown, it is a physical phenomena which is determinable for each component.

In alternate embodiments in which excitation energy is coupled to the vehicle through indirect coupling, or through direct coupling to alternate vehicle components, the transfer functions can be appropriately re-expressed in terms of transfer between the components to which the energy is induced and the components from which the attenuated energy is received.

Such frequency-dependent transfer functions can be combined or "lumped" according to well known formula often employed in Finite Element Analysis ("FEA") by mechanical engineers, or using similar formulae employed by electrical engineers. For example, if transfer function $Z^{-1}{}_A$ is in parallel with $Z^{-1}{}_B$, then the combined, "lumped" or "net" transfer function can be calculated as:

$$Z^{-1}{}_{A\|B} = \text{reciprocal of } (Z^{-1}{}_A + Z^{-1}{}_B)$$

where each transfer function $Z^{-1}$ represents a complex function varying according to frequency, time, or both.

Figure 3A:
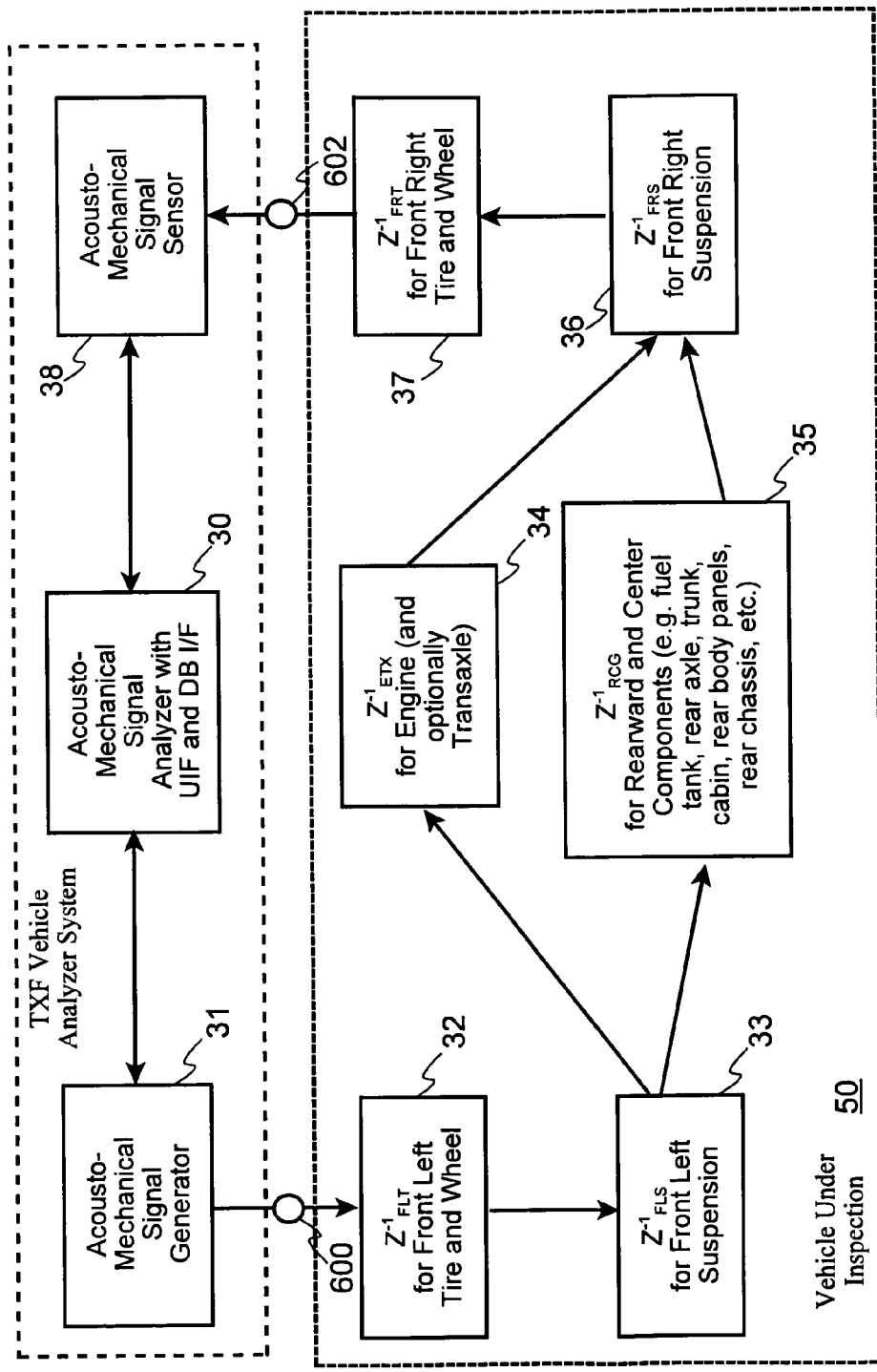
FIGS. 3a and 3b illustrate impedance models of a vehicle taken between the right front and left front wheels of a vehicle.

Turning now to FIG. 3a, a specific model of the transfer functions of the components of the vehicle as "seen" by the analyzer (30) through the front wheels (600, 602) is shown. In this configuration, the signal generator (31) induces a signal, such as a sweeping 0 Hz to 50 kHz vibrational and acoustical signal, into the front left tire, wheel and suspension. The signal will first travel in series through the tire, wheel, and suspension impedances (32, 33), then will travel in parallel through the impedances of the engine, transaxle (if front wheel or four-wheel drive) (34), and the impedances of the rearward portions of the vehicle (35), such as the fuel tank, rear axle, trunk or cargo area, rear body panels, etc., shown lumped as a single impedance (35) in this figure for simplicity. The signal then travels in series through the impedance of the front right suspension components (36), through impedance of the front right wheel and tire (37), and finally to the collection sensor, where the signal is preferably digitized and provided in data form back to the analyzer (30), such as in a "WAV" or other digital file format.

Figure 3B:
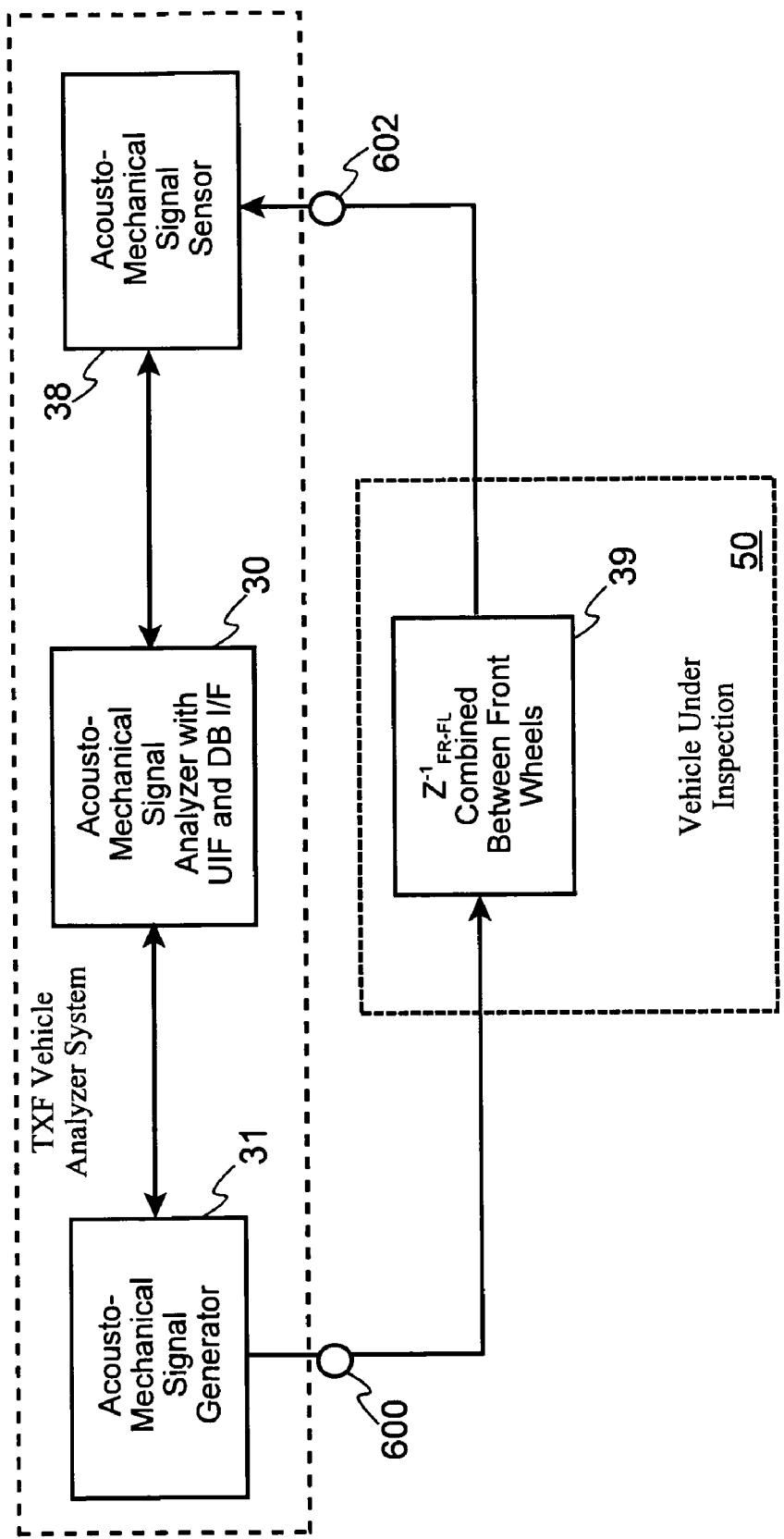

From the perspective of the analyzer, each of the component impedances of FIG. 3a need not be resolved and determined individually, but may be viewed as one "lump" transfer function (39) of the vehicle under inspection (50) taken between the two front wheels (600, 602), as shown in FIG. 3b. One must only understand that this lumped impedance is comprised of independent series and parallel related impedance, so that it is evident to the reader that a change in any one of the impedances, such as by change in mass loading (e.g. addition or subtraction of a liquid or mass to the component), will effect the overall, lumped impedance as seen by the analyzer (30).

Figure 4A:
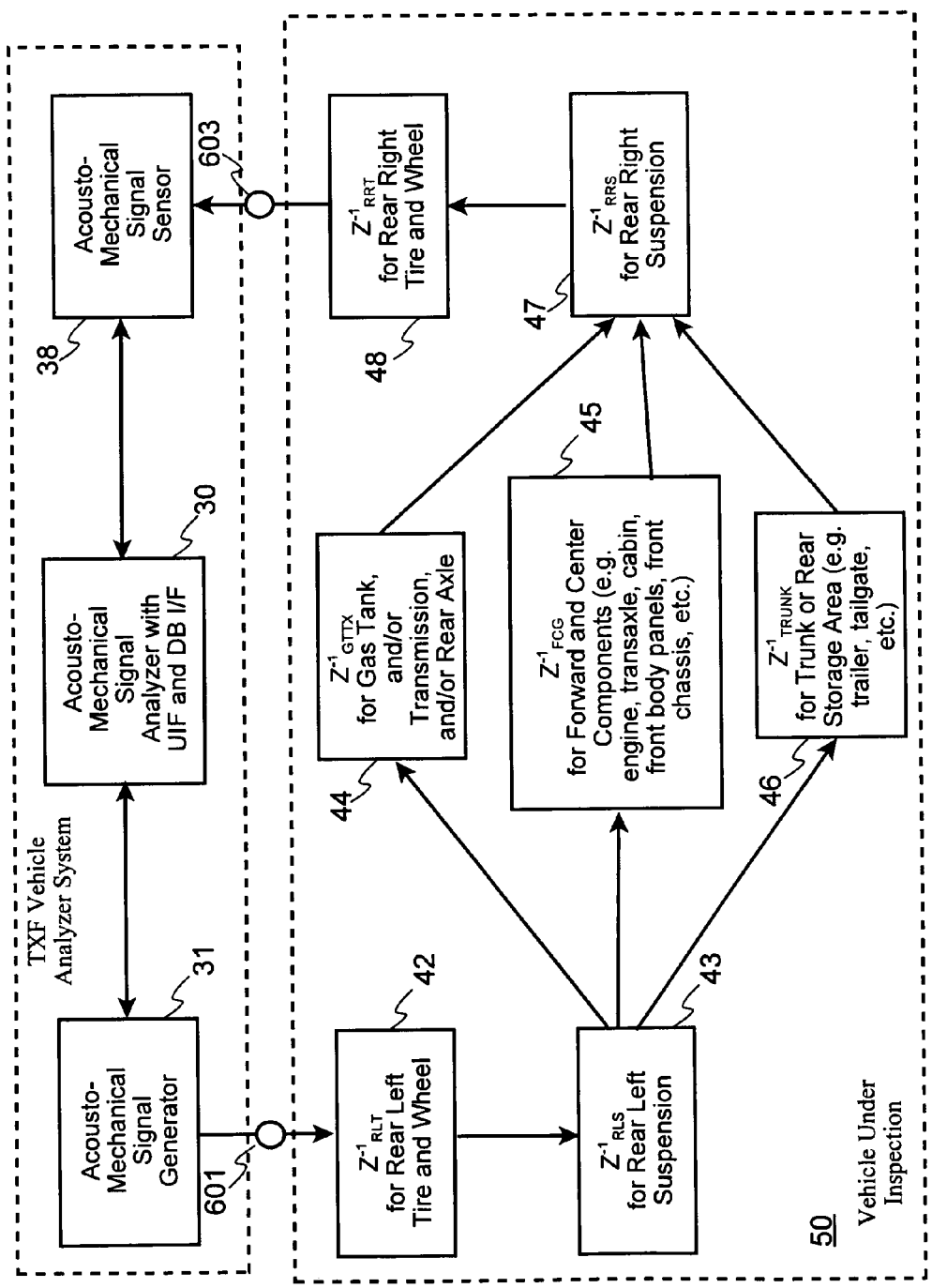
FIGS. 4a and 4b illustrate impedance models of a vehicle taken between the right rear and left rear wheels of a vehicle.
Figure 4B:
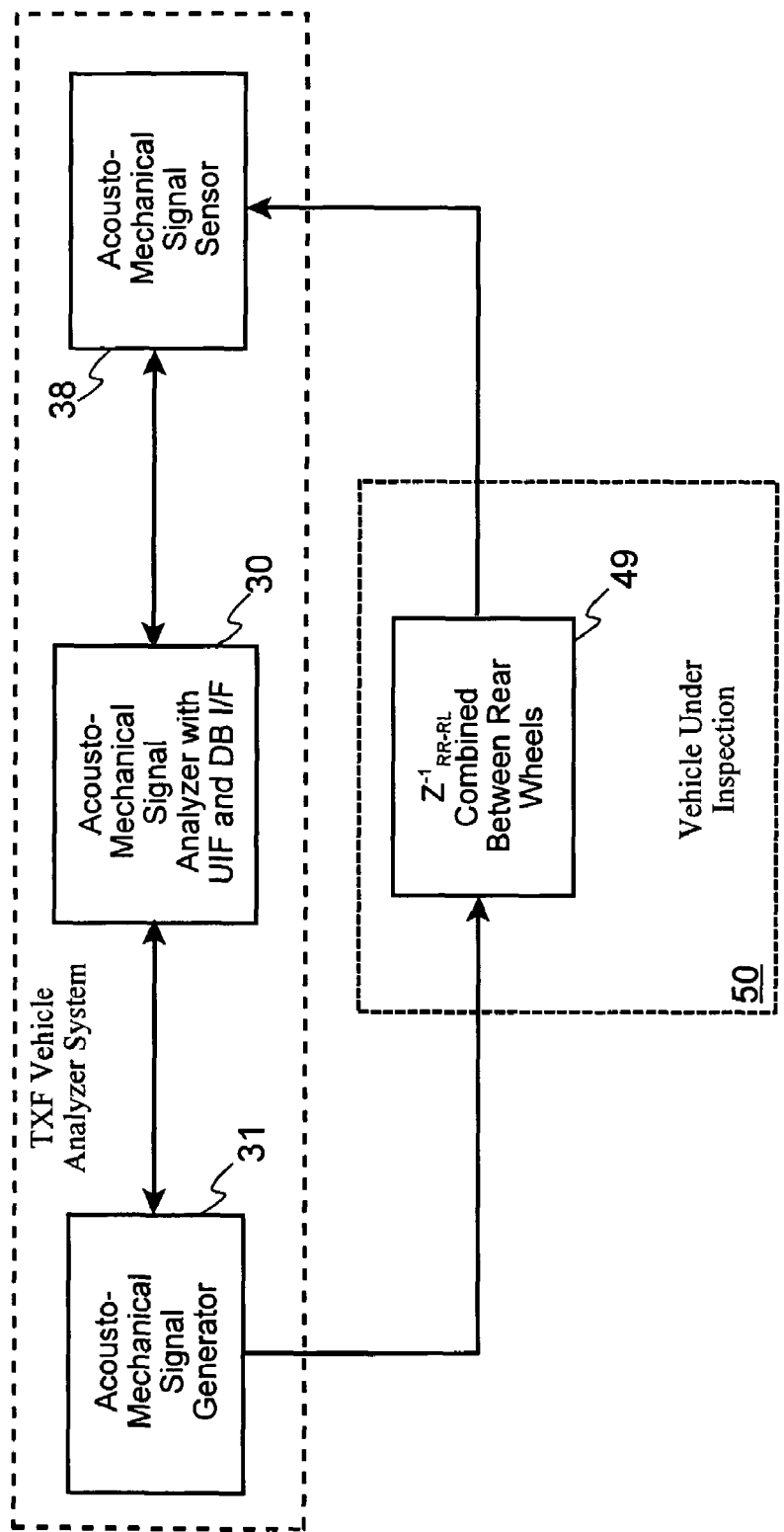

Turning to FIG. 4a, a similar depiction of the component transfer functions of the vehicle (50) are shown from the perspective of testing between the two rear wheels (601, 603). In this arrangement, the test signal travels from the signal generator (31) through series impedances for the rear left wheel and suspension (42, 43), through a number of parallel-connected impedances for the close-by components such as the gas tank, transmission, rear axle, and the trunk or cargo storage area (44, 46). The impedances of the portions of the vehicle located towards the center of the vehicle and front of the vehicle, such as the cabin, engine, etc., have been shown "lumped" (45) in this figure for simplicity, as well. The test signal then travels through the series impedances of the rear right suspension and rear right wheel (47, 48), finally returning to the sensor (38) for digitization and return to the analyzer (30). Likewise, FIG. 4b shows a "lumped" transfer function (49) as seen between the rear wheels by the test system.

Figure 6:
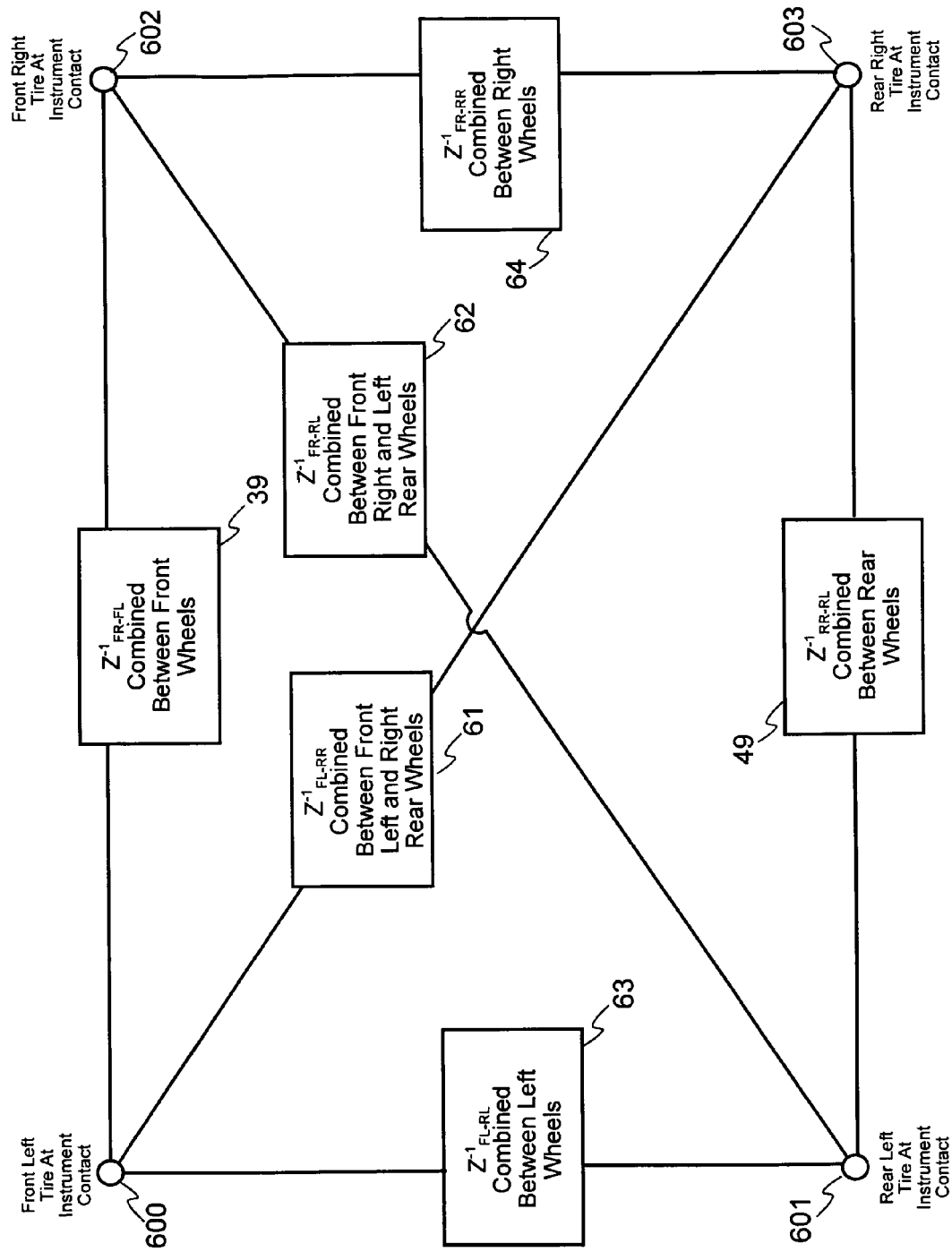
FIG. 6 shows at least six different transfer function characterizations which can be performed on a four-wheel vehicle.

The characterizations between the two front wheels and/or between the two rear wheels may be performed by the two-wheel housing configuration of the invention as shown in FIG. 7a. However, using the multiple-wheel configuration of the housing as shown in FIG. 7b, additional transfer functions can be characterized, including any or all of transfer functions between the left wheels (83), between the right wheels (64), between the front left and rear right wheels (61), and between the front right and the rear left wheels (62), as shown in FIG. 6. Each of these additional characterizations may, on some vehicles under some conditions, provide greater responsiveness to mass load changes for certain portions of the vehicle, especially those positioned directly in-line between the points of test (e.g. the tires used for signal injection and collection). For example, a characterization between the rear wheels may be most responsive to changes in the mass loading of the trunk or cargo area, but a characterization between the diagonally-related tires (e.g. front left to rear right, or front right to rear left) may be most responsive in mass loading of the cabin area. Likewise, characterization between the front wheels may be more responsive to mass loading changes in the engine compartment.

Logical Processes of the Invention

The logical processes of the invention are preferably performed in one or more software programs, either custom application programs, or applications of a readily available signal processing analysis program. An example of the latter is MatLab[™] by MathWorks of Natick, Mass. Processes and methods for generating amplitude-frequency (e.g. "frequency domain") and various time-domain visual representations of digitized or sampled signals are known within the art, and are suitable for employ in the embodiment of the present invention.

Figure 8:
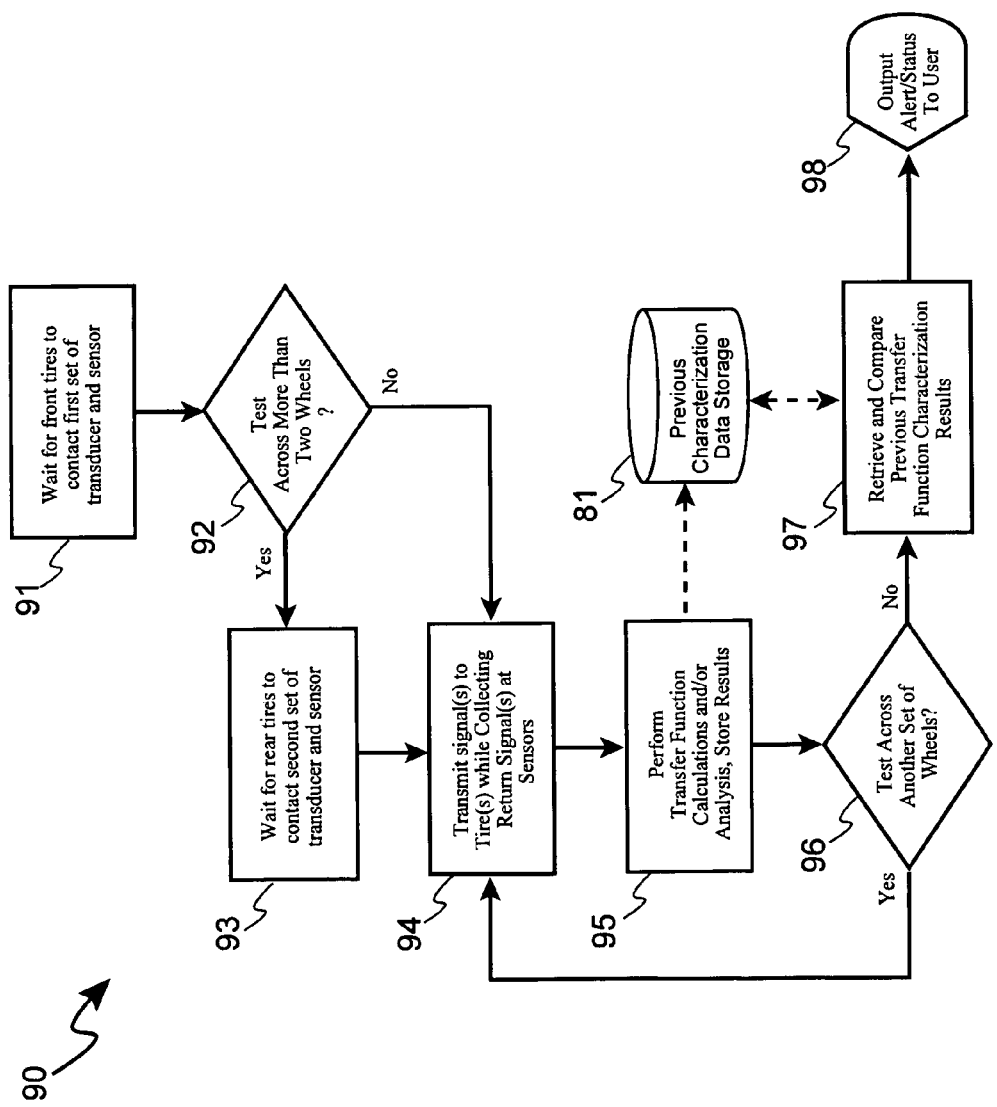
FIG. 8 sets forth a logical process according to the invention.

Turning to FIG. 8, a logical process according to the invention is shown, which begins by waiting for a set of tires, such as the front tires, to come into contact with a transducer and sensor pair (91). In configurations where more than two wheels are to be used for testing simultaneously (92), such as four wheel testing on a platform embodiment of FIG. 7b, the process then waits for the remaining vehicle wheels to come into contact with the rest of the transducers and sensors (93).

In this position, the test signal or signals are generated and transmitted into one or more wheels of the vehicle, while simultaneously collecting digital samples from one or more sensors (94). This collected data is preferably stored locally while subsequent or concurrent transfer function analysis is performed, and is preferably stored indexed to a vehicle operator identifier (e.g. name, driver's license number, passport number, etc.) and/or indexed to a vehicle identifier (e.g. make and model, VIN number, license plate number, etc.) in a remotely accessible data store or database (81). By storing the characterization data in a remotely accessible data base, this makes the information available for later comparison by the same system at the same location, or by another similar system at an alternate location, when the same vehicle or operator attempts access to the same or alternate location.

The signal generation, collection, and analysis processes are repeated until characterization across all desired sets of wheels (96) has been complete. Finally, the system accesses the remote storage (81) to determine (97) if any previous characterization data for the same vehicle or same operator is available, and if so, that data is retrieved and compared to the results of the current characterization. The two (or more) characterizations are then displayed (98) to a local (or remote) user, preferably including highlighting or denoting of areas of differences. In an alternate embodiment, the inspector may simply be given a signal to inspect further or not (e.g. green/red light type of signal).

User Alert and Display

According to an advanced embodiment of the invention, characterization results, such as a frequency-versus-magnitude plot, are shown graphically to the user, such as in a side-by-side comparison (95, 96) as shown in FIG. 9. Additionally, preferably any significant differences are automatically highlighted (97).

In alternate embodiments, if a significant difference is detected, a simple search/no-search signal may be provided to the inspector, or the comparison display may be shown using colors and overlays rather than side-by-side plots.

Suitable Computing Platform

The invention is preferably realized as a feature or addition to the software already found present on well-known computing platforms such as personal computers, web servers, and web browsers. These common computing platforms can include personal computers as well as portable computing platforms, such as personal digital assistants ("PDA"), web-enabled wireless telephones, and other types of personal information management ("PIM") devices.

Therefore, it is useful to review a generalized architecture of a computing platform which may span the range of implementation, from a high-end web or enterprise server platform, to a personal computer, to a portable PDA or web-enabled wireless phone.

Figure 2A:
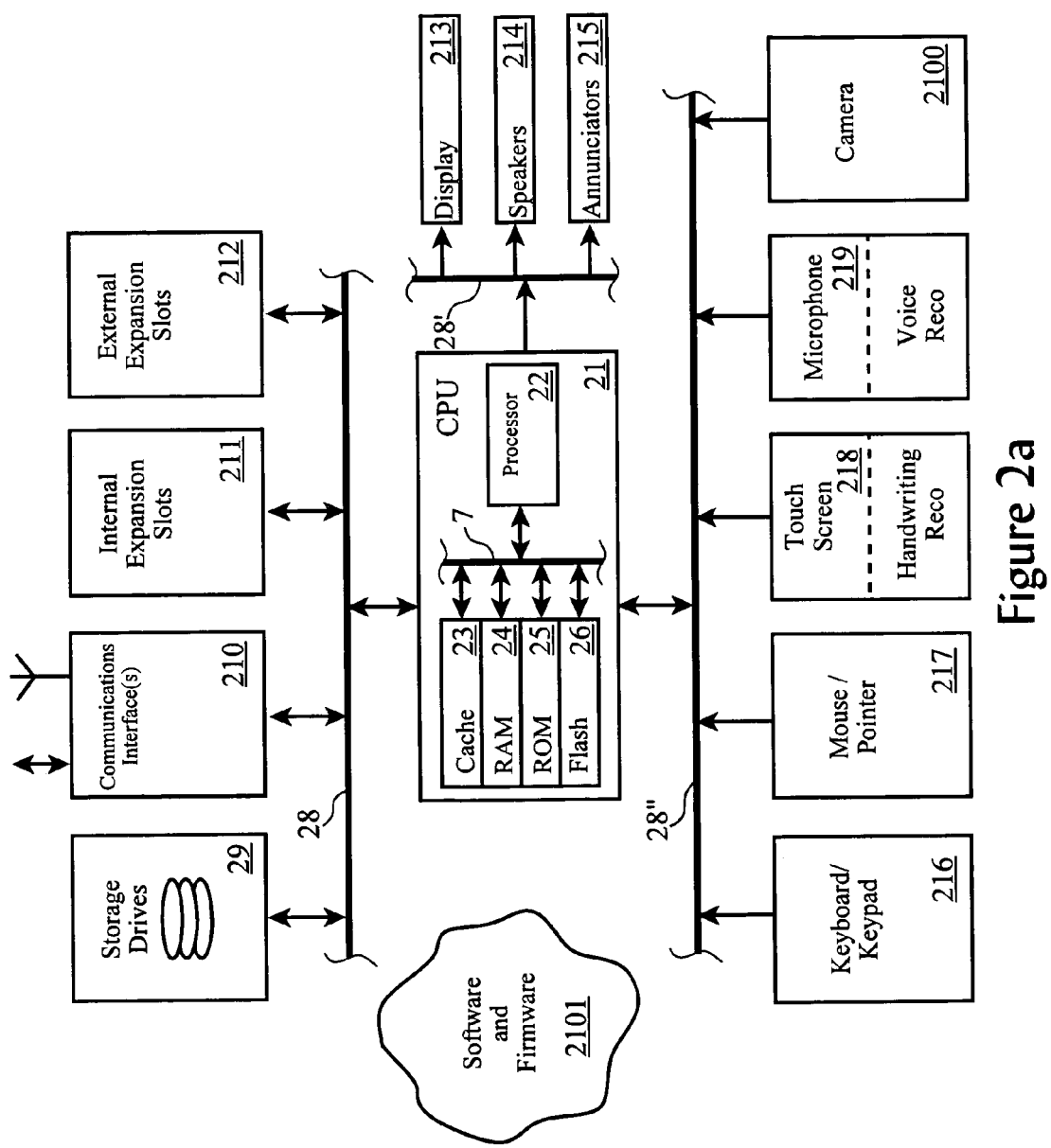
FIGS. 2a and 2b show a generalized computing platform architecture, and a generalized organization of software and firmware of such a computing platform architecture.

Turning to FIG. 2a, a generalized architecture is presented including a central processing unit (21) ("CPU"), which is typically comprised of a microprocessor (22) associated with random access memory ("RAM") (24) and read-only memory ("ROM") (25). Often, the CPU (21) is also provided with cache memory (23) and programmable FlashROM (26). The interface (27) between the microprocessor (22) and the various types of CPU memory is often referred to as a "local bus", but also may be a more generic or industry standard bus.

Many computing platforms are also provided with one or more storage drives (29), such as a hard-disk drives ("HDD"), floppy disk drives, compact disc drives (CD, CD-R, CD-RW, DVD, DVD-R, etc.), and proprietary disk and tape drives (e.g., Iomega Zip[™] and Jaz[™], Addonics SuperDisk[™], etc.). Additionally, some storage drives may be accessible over a computer network.

Many computing platforms are provided with one or more communication interfaces (210), according to the function intended of the computing platform. For example, a personal computer is often provided with a high speed serial port (RS-232, RS-422, etc.), an enhanced parallel port ("EPP"), and one or more universal serial bus ("USB") ports. The computing platform may also be provided with a local area network ("LAN") interface, such as an Ethernet card, and other high-speed interfaces such as the High Performance Serial Bus IEEE-1394.

Computing platforms such as wireless telephones and wireless networked PDA's may also be provided with a radio frequency ("RF") interface with antenna, as well. In some cases, the computing platform may be provided with an infrared data arrangement ("IrDA") interface, too.

Computing platforms are often equipped with one or more internal expansion slots (211), such as Industry Standard Architecture ("ISA"), Enhanced Industry Standard Architecture ("EISA"), Peripheral Component Interconnect ("PCI"), or proprietary interface slots for the addition of other hardware, such as sound cards, memory boards, and graphics accelerators.

Additionally, many units, such as laptop computers and PDA's, are provided with one or more external expansion slots (212) allowing the user the ability to easily install and remove hardware expansion devices, such as PCMCIA cards, SmartMedia cards, and various proprietary modules such as removable hard drives, CD drives, and floppy drives.

Often, the storage drives (29), communication interfaces (210), internal expansion slots (211) and external expansion slots (212) are interconnected with the CPU (21) via a standard or industry open bus architecture (28), such as ISA, EISA, or PCI. In many cases, the bus (28) may be of a proprietary design.

A computing platform is usually provided with one or more user input devices, such as a keyboard or a keypad (216), and mouse or pointer device (217), and/or a touch-screen display (218). In the case of a personal computer, a full size keyboard is often provided along with a mouse or pointer device, such as a track ball or TrackPoint[™]. In the case of a web-enabled wireless telephone, a simple keypad may be provided with one or more function-specific keys. In the case of a PDA, a touch-screen (218) is usually provided, often with handwriting recognition capabilities.

Additionally, a microphone (219), such as the microphone of a web-enabled wireless telephone or the microphone of a personal computer, is supplied with the computing platform. This microphone may be used for simply reporting audio and voice signals, and it may also be used for entering user choices, such as voice navigation of web sites or auto-dialing telephone numbers, using voice recognition capabilities.

Many computing platforms are also equipped with a camera device (2100), such as a still digital camera or full motion video digital camera.

One or more user output devices, such as a display (213), are also provided with most computing platforms. The display (213) may take many forms, including a Cathode Ray Tube ("CRT"), a Thin Flat Transistor ("TFT") array, or a simple set of light emitting diodes ("LED") or liquid crystal display ("LCD") indicators.

One or more speakers (214) and/or annunciators (215) are often associated with computing platforms, too. The speakers (214) may be used to reproduce audio and music, such as the speaker of a wireless telephone or the speakers of a personal computer. Annunciators (215) may take the form of simple beep emitters or buzzers, commonly found on certain devices such as PDAs and PIMs.

These user input and output devices may be directly interconnected (28', 28") to the CPU (21) via a proprietary bus structure and/or interfaces, or they may be interconnected through one or more industry open buses such as ISA, EISA, PCI, etc.

The computing platform is also provided with one or more software and firmware (2101) programs to implement the desired functionality of the computing platforms.

Figure 2B:
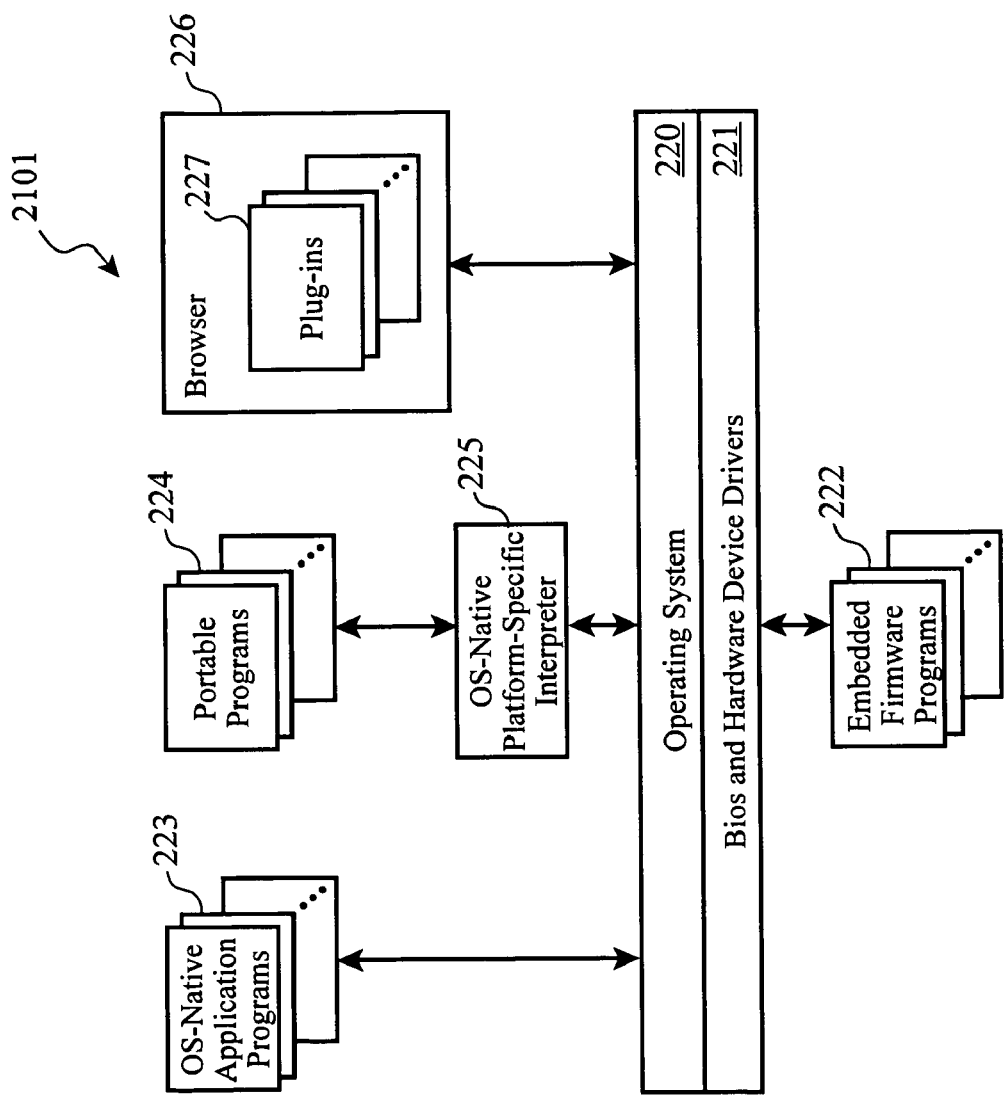

Turning to now FIG. 2b, more detail is given of a generalized organization of software and firmware (2101) on this range of computing platforms. One or more operating system ("OS") native application programs (223) may be provided on the computing platform, such as word processors, spreadsheets, contact management utilities, address book, calendar, email client, presentation, financial and bookkeeping programs.

Additionally, one or more "portable" or device-independent programs (224) may be provided, which must be interpreted by an OS-native platform-specific interpreter (225), such as Java[™] scripts and programs.

Often, computing platforms are also provided with a form of web browser or micro-browser (226), which may also include one or more extensions to the browser such as browser plug-ins (227).

The computing device is often provided with an operating system (220), such as Microsoft Windows[™], UNIX, IBM OS/2[™], IBM AIX[™], open source LINUX, Apple's MAC OS[™], or other platform specific operating systems. Smaller devices such as PDA's and wireless telephones may be equipped with other forms of operating systems such as real-time operating systems ("RTOS") or Palm Computing's PalmOS[™].

A set of basic input and output functions ("BIOS") and hardware device drivers (22 1) are often provided to allow the operating system (220) and programs to interface to and control the specific hardware functions provided with the computing platform.

Additionally, one or more embedded firmware programs (222) are commonly provided with many computing platforms, which are executed by onboard or "embedded" microprocessors as part of the peripheral device, such as a micro controller or a hard drive, a communication processor, network interface card, or sound or graphics card.

As such, FIGS. 2a and 2b describe in a general sense the various hardware components, software and firmware programs of a wide variety of computing platforms, including but not limited to personal computers, PDAs, PIMs, web-enabled telephones, and other appliances such as WebTV[™] units. It will be readily recognized by those skilled in the art that the methods and processes described herein may be alternatively realized as hardware functions, in part or in whole, without departing from the spirit and scope of the invention.

CONCLUSION

Certain example embodiments have been provided to illustrate the invention. It will be recognized by those skilled in the art, however, that these example embodiments do not represent the scope of the present invention, and that certain variations and modifications may be made without departing from the spirit and scope of the invention.

I claim:

1. A system comprising:
    an acoustic excitation energy transmitter configured to directly couple an acoustic signal to a first tire of a first vehicle;
    a collector configured to receive attenuated acoustic energy transferred through said first vehicle from said transmitter to a second tire of said first vehicle;
    an analyzer configured to determine a first set of energy transfer characteristics of said first vehicle by analysis of said excitation energy and said received attenuated acoustic energy;
    a storage memory for recording said first set of energy transfer characteristics; and
    a comparator configured to produce a comparison of said first set of energy transfer characteristics with a second set of energy transfer characteristics, said second set comprising energy transfer characteristics collected from said first vehicle or from a second vehicle of a same make and model as said first vehicle.

2. The system as set forth in claim 1 wherein said comparison comprises a graphical depiction of a comparison of said first and second sets of energy transfer characteristics.

3. The system as set forth in claim 1 further comprising a user alert means responsive to said comparator indicating a threshold level of difference between said first and second sets of energy transfer characteristics.

4. The system as set forth in claim 1 further comprising a previous record retriever configured to retrieve a second set of energy transfer characteristics according to an identifier of said vehicle.

5. The system as set forth in claim 4 wherein said identifier comprises a Vehicle Identification Number.

6. The system as set forth in claim 4 wherein said identifier comprises a license plate number.

7. The system as set forth in claim 4 wherein said identifier comprises a make and model indicator.

8. The system as set forth in claim 1 wherein said analyzer and comparator are configured to perform signal amplitude analysis.

9. The system as set forth in claim 1 wherein said analyzer and comparator are configured to perform frequency-domain analysis.

10. The system as set forth in claim 1 wherein said direct coupling comprises a drive-over housing which contacts at least one wheel of said first vehicle.

11. The system as set forth in claim 1 wherein said collector comprises a vibration sensor.

12. The system as set forth in claim 1 wherein said collector comprises a microphone.

13. The system as set forth in claim 1 wherein said excitation energy comprises a vibrational signal having a frequency between approximately 1 cycle per second and 50 cycles per second, inclusive.

14. The system as set forth in claim 1 wherein said excitation energy comprises a vibrational signal having a frequency between approximately 50 cycles per second and 20,000 cycles per second, inclusive.

15. The system as set forth in claim 1 wherein said excitation energy comprises a vibrational signal having a frequency greater than approximately 20,000 cycles per second.

* * * * *